United States Patent
Shah et al.

(10) Patent No.: US 8,604,195 B2
(45) Date of Patent: Dec. 10, 2013

(54) SUBSTITUTED BICYCLIC PIPERIDINYL- AND PIPERAZINYL-SULFONAMIDES USEFUL TO INHIBIT 11β-HYDROXYSTEROID DEHYDROGENASE TYPE-1

(75) Inventors: Unmesh Shah, Green Brook, NJ (US); Craig D. Boyle, Branchburg, NJ (US); Samuel Chackalamannil, Califon, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 553 days.

(21) Appl. No.: 12/672,825

(22) PCT Filed: Aug. 12, 2008

(86) PCT No.: PCT/US2008/009607
§ 371 (c)(1),
(2), (4) Date: Nov. 23, 2010

(87) PCT Pub. No.: WO2009/023180
PCT Pub. Date: Feb. 19, 2009

(65) Prior Publication Data
US 2011/0059929 A1    Mar. 10, 2011

Related U.S. Application Data

(60) Provisional application No. 60/955,977, filed on Aug. 15, 2007.

(51) Int. Cl.
*C07D 451/06* (2006.01)
*C07D 471/08* (2006.01)
*A61K 31/46* (2006.01)
*A61K 31/529* (2006.01)

(52) U.S. Cl.
USPC ............ 544/349; 546/125; 514/304; 514/249

(58) Field of Classification Search
USPC .................... 544/349; 546/125; 514/249, 304
See application file for complete search history.

(56) References Cited

U.S. PATENT DOCUMENTS

2004/0186135 A1    9/2004    Dolle et al.
2004/0254218 A1    12/2004   Bourdonnec et al.

FOREIGN PATENT DOCUMENTS

WO    WO2007024651 A1 *    3/2007

* cited by examiner

*Primary Examiner* — David K O Dell
(74) *Attorney, Agent, or Firm* — Richard S. Parr; Catherine D. Fitch

(57) ABSTRACT

In its many embodiments, the present invention relates to a novel class of substituted bicyclic piperidinyl- and piperazinylsulfonamide compounds useful to inhibit 11β-hydroxysteroid dehydrogenase type-I, pharmaceutical compositions containing the compounds, and methods of treatment, prevention, inhibition, or amelioration of one or more conditions associated with the expression of 11β-hydroxysteroid dehydrogenase type-I using such compounds or pharmaceutical compositions.

2 Claims, No Drawings

SUBSTITUTED BICYCLIC PIPERIDINYL- AND PIPERAZINYL-SULFONAMIDES USEFUL TO INHIBIT 11β-HYDROXYSTEROID DEHYDROGENASE TYPE-1

RELATED APPLICATIONS

This application claims benefit of provisional application U.S. Ser. No. 60/955,977, filed Aug. 15, 2007, herein incorporated by reference.

FIELD OF THE INVENTION

The present invention relates to relates to substituted bicyclic piperidinyl- and piperazinylsulfonamide compounds useful to inhibit 11β-hydroxysteroid dehydrogenase type-I, pharmaceutical compositions containing the compounds, and methods of treatment, prevention, inhibition, or amelioration of one or more conditions associated with the expression of 11β-hydroxysteroid dehydrogenase type-I using such compounds or pharmaceutical compositions.

BACKGROUND OF THE INVENTION

Glucocorticoids are steroid hormones that regulate many metabolic and homeostatic processes, including fat metabolism, function and distribution. Glucocorticoids also have profound and diverse physiological effects on development, neurobiology, inflammation, blood pressure, metabolism and programmed cell death.

Glucocorticoid action is dependent on the following factors: 1) circulating levels of glucocorticoid; 2) protein binding of glucocorticoids in circulation; 3) intracellular receptor density inside target tissues; and 4) tissue-specific pre-receptor metabolism by glucocorticoid-activating and glucocorticoid-inactivating enzymes collectively known as 11-beta-hydroxysteroid dehydrogenase (11-β-HSD). Two distinct isozymes of 11-β-HSD have been cloned and characterized. These two isozymes, known as 11-β-HSD type I and 11-β-HSD type II, respectively, catalyze the interconversion of active and inactive forms of various glucocorticoids. For example, in humans, the primary endogenously-produced glucocorticoid is cortisol. 11-β-HSD type I and 11-β-HSD type II catalyze the interconversion of hormonally active cortisol and inactive cortisone. 11-β-HSD type I is widely distributed in human tissues and its expression has been detected in lung, testis, central nervous system and most abundantly in liver and adipose tissue. Conversely, 11-β-HSD type II expression is found mainly in kidney, placenta, colon and salivary gland tissue.

Up-regulation of 11-β-HSD type I can lead to elevated cellular glucocorticoid levels and amplified glucocorticoid activity. This, in turn, can lead to increased hepatic glucose production, adipocyte differentiation and insulin resistance. In type II diabetes, insulin resistance is a significant pathogenic factor in the development of hyperglycemia. Persistent or uncontrolled hyperglycemia in both type 1 and type 2 diabetes has been associated with increased incidence of macrovascular and/or microvascular complications including atherosclerosis, coronary heart disease, peripheral vascular disease, stroke, nephropathy, neuropathy and retinopathy. Insulin resistance, even in the absence of profound hyperglycemia, is a component also of metabolic syndrome, which is characterized by elevated blood pressure, high fasting blood glucose levels, abdominal obesity, increased triglyceride levels and/or decreased HDL cholesterol. Further, glucocorticoids are known to inhibit the glucose-stimulated secretion of insulin from pancreatic beta-cells. Inhibition of 11-β-HSD type I is, therefore, expected to be beneficial in the treatment of metabolic syndromes, obesity, obesity-related disorders, hypertension, atherosclerosis, lipid disorders, type-II diabetes, insulin resistance, pancreatitis and associated conditions.

Mild cognitive impairment is a common feature of aging that may be ultimately related to the progression of dementia. Chronic exposure to glucocorticoid excess in certain brain subregions has been proposed to contribute to the decline of cognitive function. Inhibition of 11-β-HSD type I is expected to reduce exposure to glucocorticoids in the brain and protect against deleterious glucocorticoid effects on neuronal function, including cognitive impairment, dementia and/or depression, especially in connection with Alzheimer's Disease.

Glucocorticoids also have a role in corticosteroid-induced glaucoma. This particular pathology is characterized by a significant increase in intraocular pressure, which unresolved can lead to partial visual field loss and eventually blindness. Inhibition of 11-β-HSD type I is expected to reduce local glucocorticoid concentrations and, thus, intra-ocular pressure, producing beneficial effects in the management of glaucoma and other visual disorders.

Finally, glucocorticoids can have adverse effects on skeletal tissues. Continued exposure to excess glucocorticoids can produce osteoporosis and increased risk of fractures. Inhibition of 11-β-HSD type I should reduce local glucocorticoid concentration within osteoblasts and osteoclasts, producing beneficial effects for management of bone disease, including osteoporosis.

In view of the foregoing, there is a clear and continuing need for new compounds that target 11-β-HSD type I.

SUMMARY OF THE INVENTION

In its many embodiments, the present invention provides a novel class of heterocyclic compounds as inhibitors of 11β-hydroxysteroid dehydrogenase type-I, pharmaceutical compositions containing the compounds, and methods of treatment, prevention, inhibition, or amelioration of one or more conditions associated with the expression of 11β-hydroxysteroid dehydrogenase type-I using such compounds or pharmaceutical compositions.

In one aspect, the present application discloses a compound, or a pharmaceutically acceptable salt, solvate, ester or prodrug of said compound, said compound having the general structure shown in Formula I:

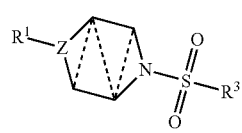

I wherein:
Z represents $CR^2$ or N;
$R^1$ represents H, alkyl, cycloalkyl, aryl, aralkyl, hydroxyl, alkoxy, aryloxy, heteroaryloxy or alkoxycarbonyl;
$R^2$ represents H, alkyl, cycloalkyl, aryl, aralkyl, hydroxyl, alkoxy, aryloxy, heteroaryloxy or alkoxycarbonyl; or
$R^1$ and $R^2$ together optionally represent =O, =S or =$NOR^4$;
$R^3$ represents para-$R^5$-phenyl;
$R^4$ represents H, alkyl or aralkyl;
$R^5$ represents alkyl other than methyl, hydroxyalkyl, alkoxyalkyl, cycloalkyl, aryl, heteroaryl or heterocyclyl;
and wherein each ----- represents an alkylene bridge provided that the compound has only one such alkylene bridge; with the exception of the following compounds:
6-(4-(5-benzyl-2,5-diazabicyclo[2.2.1]heptan-2-ylsulfonyl)phenyl)-3-methyl-1-propyl-1H-pyrrolo[3,2-d]pyrimidine-2,4-(3H,5H)-dione;

6-(4-(5-benzyl-2,5-diazabicyclo[2.2.1]heptan-2-ylsulfonyl)
phenyl)-1,3-diethyl-1H-pyrrolo[3,2-d]pyrimidine-2,4-
(3H,5H)-dione;
6-(4-(5-benzyl-2,5-diazabicyclo[2.2.1]heptan-2-ylsulfonyl)
phenyl)-1,3-dimethyl-1H-pyrrolo[3,2-d]pyrimidine-2,4-
(3H,5H)-dione;
(R)-1-(4-((1S,4S)-5-(4-tert-butylphenylsulfonyl)-2,5-diaz-
abicyclo[2.2.1]heptan-2-yl)pyrimidin-2-yl)ethanol;
3-(2,5-diazabicyclo[2.2.1]heptan-2-ylsulfonyl)-4-(3,5-
dichlorophenoxy)benzonitrile; and
N-((8-(4-chloro-2-(pyridin-3-yl)phenylsulfonyl)-3-ethyl-8-
azabicyclo[3.2.1]octan-3-yl)methyl)-2,2,2-trifluoroetha-
namine.

In addition, the present invention also includes a compound of the formula:

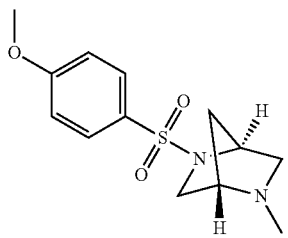 [SMILES: COc1ccc(S(=O)(=O)N2C[C@@H]3C[C@H]2CN3C)cc1]

or

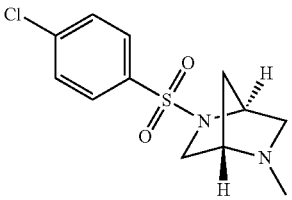 [SMILES: CN1C[C@@H]2C[C@H]1CN2S(=O)(=O)c1ccc(Cl)cc1]

or a pharmaceutically acceptable salt, solvate, ester or prodrug thereof.

The compounds of Formula I, including those excluded, and the two additional compounds mentioned above, as well as salts, solvates, esters and prodrugs thereof, are inhibitors of 11β-hydroxysteroid dehydrogenase type-I, and can be used in the treatment of metabolic syndromes, obesity, obesity-related disorders, hypertension, atherosclerosis, lipid disorders, type-II diabetes, insulin resistance, pancreatitis and associated conditions.

Alternatively, the present invention provides for a method for treating a metabolic syndrome in a patient in need thereof which comprises administering to said patient a therapeutically effective amount of at least one compound of the Formula I:

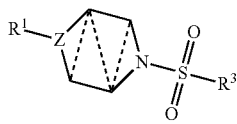

or a pharmaceutically acceptable salt, solvate, ester or prodrug thereof;
wherein:
Z represents $CR^2$ or N;
$R^1$ represents H, alkyl, cycloalkyl, aryl, aralkyl, hydroxyl, alkoxy, aryloxy, heteroaryloxy or alkoxycarbonyl;
$R^2$ represents H, alkyl, cycloalkyl, aryl, aralkyl, hydroxyl, alkoxy, aryloxy, heteroaryloxy or alkoxycarbonyl; or
$R^1$ and $R^2$ together optionally represent =O, =S or =$NOR^4$;
$R^3$ represents aryl or heteroaryl;
$R^4$ represents H, alkyl or aralkyl;
and wherein each ----- represents an alkylene bridge provided that the compound has only one such alkylene bridge.

A further embodiment of the present invention is a method for treating obesity or an obesity-related disorder in a patient in need thereof which comprises administering to said patient a therapeutically effective amount of at least one compound of the Formula I:

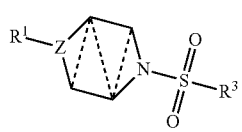

or a pharmaceutically acceptable salt, solvate, ester or prodrug thereof;
wherein:
Z represents $CR^2$ or N;
$R^1$ represents H, alkyl, cycloalkyl, aryl, aralkyl, hydroxyl, alkoxy, aryloxy, heteroaryloxy or alkoxycarbonyl;
$R^2$ represents H, alkyl, cycloalkyl, aryl, aralkyl, hydroxyl, alkoxy, aryloxy, heteroaryloxy or alkoxycarbonyl; or
$R^1$ and $R^2$ together optionally represent =O, =S or =$NOR^4$;
$R^3$ represents aryl or heteroaryl;
$R^4$ represents H, alkyl or aralkyl;
and wherein each ----- represents an alkylene bridge provided that the compound has only one such alkylene bridge.

Another embodiment of the present invention is a method for treating type-II diabetes in a patient in need thereof which comprises administering to said patient a therapeutically effective amount of at least one compound of the Formula I:

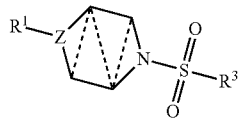

or a pharmaceutically acceptable salt, solvate, ester or prodrug thereof;
wherein:
Z represents $CR^2$ or N;
$R^1$ represents H, alkyl, cycloalkyl, aryl, aralkyl, hydroxyl, alkoxy, aryloxy, heteroaryloxy or alkoxycarbonyl;
$R^2$ represents H, alkyl, cycloalkyl, aryl, aralkyl, hydroxyl, alkoxy, aryloxy, heteroaryloxy or alkoxycarbonyl; or
$R^1$ and $R^2$ together optionally represent =O, =S or =$NOR^4$;
$R^3$ represents aryl or heteroaryl;
$R^4$ represents H, alkyl or aralkyl;
and wherein each ----- represents an alkylene bridge provided that the compound has only one such alkylene bridge.

Another embodiment of the present invention is a method for treating atherosclerosis in a patient in need thereof which comprises administering to said patient a therapeutically effective amount of at least one compound of the Formula I:

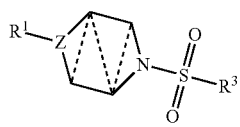

or a pharmaceutically acceptable salt, solvate, ester or prodrug thereof;
wherein:
  Z represents CR² or N;
  R¹ represents H, alkyl, cycloalkyl, aryl, aralkyl, hydroxyl, alkoxy, aryloxy, heteroaryloxy or alkoxycarbonyl;
  R² represents H, alkyl, cycloalkyl, aryl, aralkyl, hydroxyl, alkoxy, aryloxy, heteroaryloxy or alkoxycarbonyl; or
  R¹ and R² together optionally represent =O, =S or =NOR⁴;
  R³ represents aryl or heteroaryl;
  R⁴ represents H, alkyl or aralkyl;
and wherein each ----- represents an alkylene bridge provided that the compound has only one such alkylene bridge.

DETAILED DESCRIPTION

In one embodiment, the present invention discloses certain heterocyclic compounds which are represented by structural Formula I, or a pharmaceutically acceptable salt, solvate, ester or prodrug thereof, wherein the various moieties are as described above.

In another embodiment, the present invention embodies compounds of the Formula I, wherein:
  Z represents CR² or N;
  R¹ represents H, alkyl, cycloalkyl, aryl, aralkyl, hydroxyl, alkoxy, heteroaryloxy or alkoxycarbonyl;
  R² represents H, alkyl, aryl, aralkyl, hydroxyl, alkoxy or heteroaryloxy; or
  R¹ and R² together optionally represent =O or =NOR⁴;
  R³ represents aryl;
  R⁴ represents H, alkyl or aralkyl;
and wherein each ----- represents a methylene or ethylene bridge provided that the compound has only one such methylene or ethylene bridge.

In another embodiment, the present invention relates to compounds of the formula II:

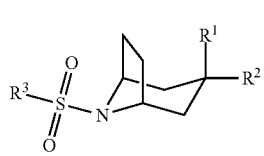

wherein R¹, R² and R³ are as defined above;
or pharmaceutically acceptable salts, solvates, esters and prodrugs thereof.

In another embodiment, the present invention relates to compounds of the formula III:

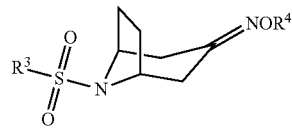

wherein R³ and R⁴ are as defined above;
or pharmaceutically acceptable salts, solvates, esters and prodrugs thereof.

In another embodiment, the present invention relates to compounds of the formula IV:

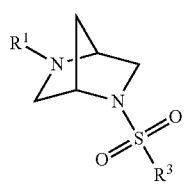

wherein R¹, R² and R³ are as defined above;
or pharmaceutically acceptable salts, solvates, esters and prodrugs thereof.

In another embodiment, the present invention relates to compounds of the formula V:

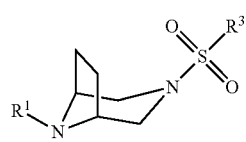

wherein A¹, R² and R³ are as defined above;
or pharmaceutically acceptable salts, solvates, esters and prodrugs thereof.

Table 1 shows structures of representative compounds of this invention. The table and the compounds therein are not intended, nor should they be construed, to limit this invention in any manner whatsoever.

TABLE 1

| COMPOUND NO. | STRUCTURE |
|---|---|
| 1 | 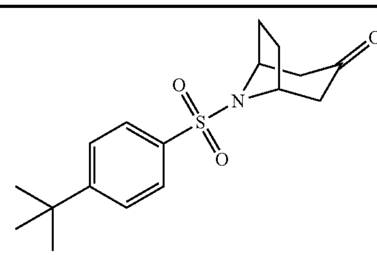 |

TABLE 1-continued
| COMPOUND NO. | STRUCTURE |
|---|---|
| 2 | 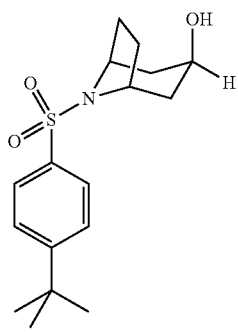 [SMILES: CC(C)(C)c1ccc(S(=O)(=O)N2C3CCC2CC(O)C3)cc1] |
| 3 | 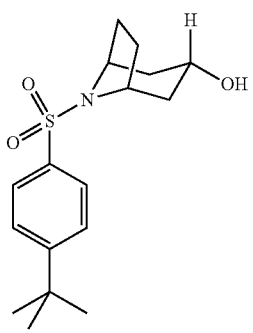 [SMILES: CC(C)(C)c1ccc(S(=O)(=O)N2C3CCC2CC(O)C3)cc1] |
| 4 | 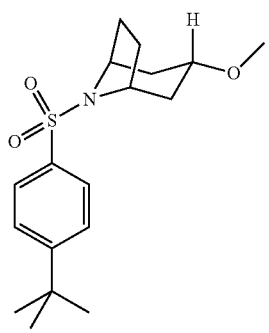 [SMILES: COC1CC2CCC(C1)N2S(=O)(=O)c1ccc(C(C)(C)C)cc1] |
| 5 | 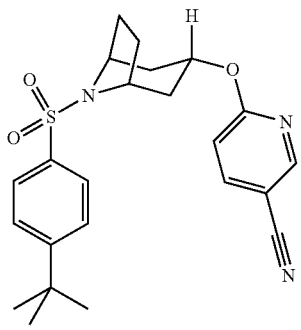 [SMILES: CC(C)(C)c1ccc(S(=O)(=O)N2C3CCC2CC(Oc2ccc(C#N)cn2)C3)cc1] |
| 6 | 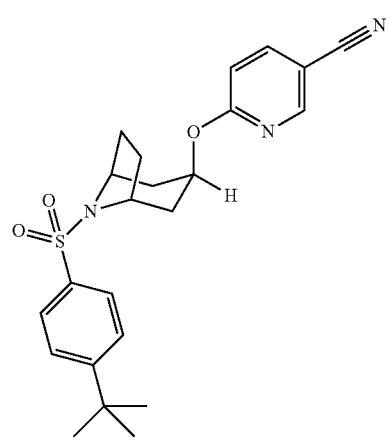 [SMILES: CC(C)(C)c1ccc(S(=O)(=O)N2C3CCC2CC(Oc2ccc(C#N)cn2)C3)cc1] |
| 7 | 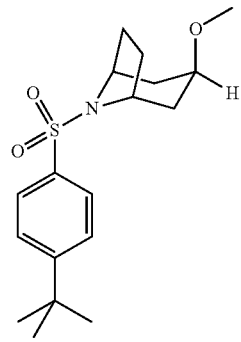 [SMILES: COC1CC2CCC(C1)N2S(=O)(=O)c1ccc(C(C)(C)C)cc1] |
| 8 | 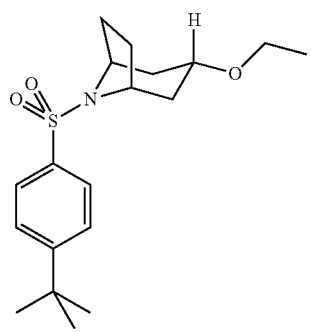 [SMILES: CCOC1CC2CCC(C1)N2S(=O)(=O)c1ccc(C(C)(C)C)cc1] |
| 9 | 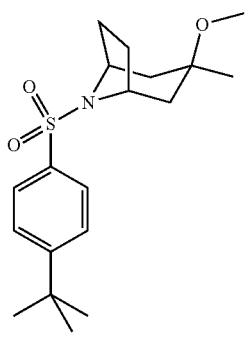 [SMILES: COC1(C)CC2CCC(C1)N2S(=O)(=O)c1ccc(C(C)(C)C)cc1] |

TABLE 1-continued

| COMPOUND NO. | STRUCTURE |
|---|---|
| 10 | (structure) |
| 11 | (structure) |
| 12 | (structure) |
| 13 | (structure) |
| 14 | (structure) |
| 15 | (structure) |
| 16 | (structure) |
| 17 | (structure) |
| 18 | (structure) |

TABLE 1-continued
| COMPOUND NO. | STRUCTURE |
|---|---|
| 19 | 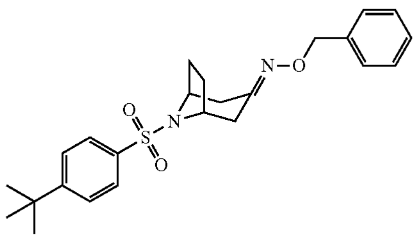 [SMILES: CC(C)(C)c1ccc(S(=O)(=O)N2C3CCC2CC(=NOCc2ccccc2)C3)cc1] |
| 20 | 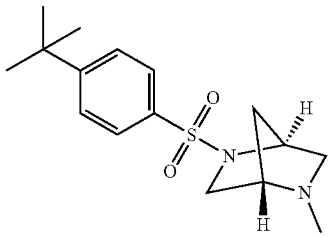 [SMILES: CN1C[C@@H]2C[C@H]1CN2S(=O)(=O)c1ccc(C(C)(C)C)cc1] |
| 21 | 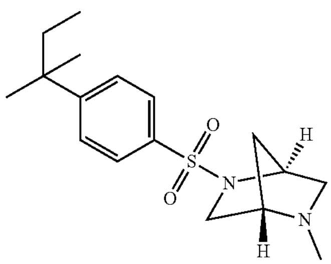 [SMILES: CCC(C)(C)c1ccc(S(=O)(=O)N2C[C@@H]3C[C@H]2CN3C)cc1] |
| 22 | 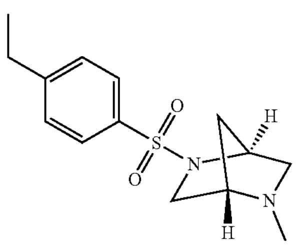 [SMILES: CCc1ccc(S(=O)(=O)N2C[C@@H]3C[C@H]2CN3C)cc1] |
| 23 | 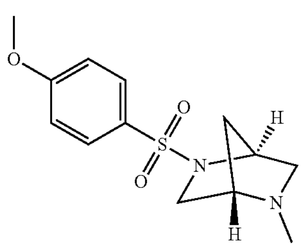 [SMILES: COc1ccc(S(=O)(=O)N2C[C@@H]3C[C@H]2CN3C)cc1] |
| 24 | 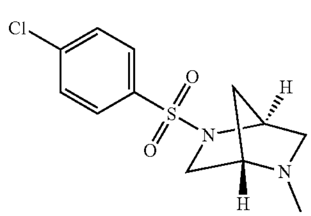 [SMILES: CN1C[C@@H]2C[C@H]1CN2S(=O)(=O)c1ccc(Cl)cc1] |
TABLE 1-continued
| COMPOUND NO. | STRUCTURE |
|---|---|
| 25 | |
| 26 | |
| 27 | 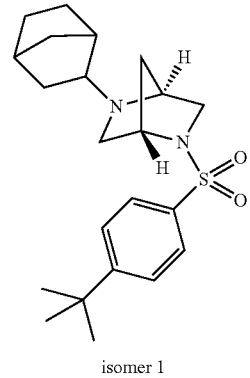 [SMILES: CC(C)(C)c1ccc(S(=O)(=O)N2C[C@@H]3C[C@H]2CN3C2CC3CCC2C3)cc1]<br>isomer 1 |
| 28 | 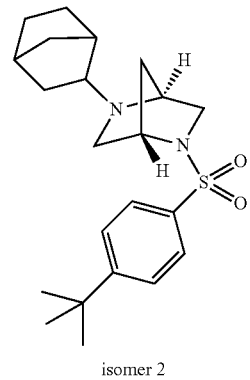 [SMILES: CC(C)(C)c1ccc(S(=O)(=O)N2C[C@@H]3C[C@H]2CN3C2CC3CCC2C3)cc1]<br>isomer 2 |

TABLE 1-continued

| COMPOUND NO. | STRUCTURE |
| --- | --- |
| 29 | (cyclohexyl-N, bicyclic diamine with H stereochemistry, N-sulfonyl-4-tert-butylphenyl) |
| 30 | (cyclopentyl-N, bicyclic diamine with H stereochemistry, N-sulfonyl-4-tert-butylphenyl) |
| 31 | (tert-butoxycarbonyl-N, bicyclic diamine, N-sulfonyl-4-tert-butylphenyl) |
| 32 | (NH, bicyclic diamine, N-sulfonyl-4-tert-butylphenyl) |
| 33 | (N-methyl, bicyclic diamine, N-sulfonyl-4-tert-butylphenyl) |
| 34 | (cyclopentyl-N, bicyclic diamine, N-sulfonyl-4-tert-butylphenyl) |

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

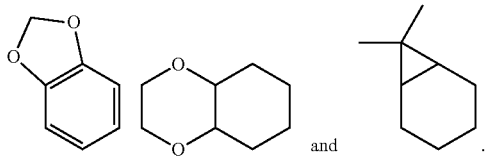

and

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

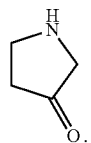

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

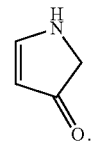

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

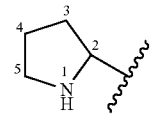

there is no —OH attached directly to carbons marked 2 and 5.

It should also be noted that tautomeric forms such as, for example, the moieties:

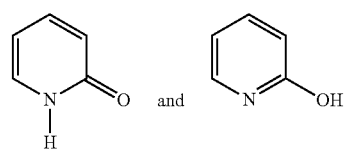 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino ($C_1$-$C_4$)alkyl or mono-N-or di-N,N-($C_1$-$C_6$)alkylaminoalkyl, —C(Y$^4$)Y$^5$ wherein Y$^4$ is H or methyl and Y$^5$ is mono-N— or di-N,N($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The compounds according to the invention have pharmacological properties; in particular, the compounds of Formula I can be inhibitors of 11β-hydroxysteroid dehydrogenase type I.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "obesity-related disorder" as used herein refers to: (i) disorders which result from a patient having a BMI of 25 or greater; and (ii) eating disorders and other disorders associated with excessive food intake. Non-limiting examples of an obesity-related disorder include edema, shortness of breath, sleep apnea, skin disorders and high blood pressure.

The term "metabolic syndrome" as used herein, refers to a set of risk factors that make a patient more succeptible to cardiovascular disease and/or type 2 diabetes. A patient is said to have metabolic syndrome if the patient has one or more of the following five risk factors:
1) central/abdominal obesity as measured by a waist circumference of greater than 40 inches in a male and greater than 35 inches in a female;
2) a fasting triglyceride level of greater than or equal to 150 mg/dL;
3) an HDL cholesterol level in a male of less than 40 mg/dL or in a female of less than 50 mg/dL;
4) blood pressure greater than or equal to 130/85 mm Hg; and
5) a fasting glucose level of greater than or equal to 110 mg/dL.

A preferred dosage is about 0.001 to 5 mg/kg of body weight/day of the compound of Formula I. An especially preferred dosage is about 0.01 to 5 mg/kg of body weight/day of a compound of Formula I, or a pharmaceutically acceptable salt, solvate, ester or prodrug of said compound.

In one embodiment, the present invention provides methods for treating a Condition in a patient, the method comprising administering to the patient one or more compounds of Formula I, or a pharmaceutically acceptable salt, solvate, ester or prodrug thereof and at least one additional therapeutic agent that is not a compound of Formula I, wherein the amounts administered are together effective to treat or prevent a Condition.

Non-limiting examples of additional therapeutic agents useful in the present methods for treating or preventing a Condition include, anti-obesity agents, antidiabetic agents, any agent useful for treating metabolic syndrome, any agent useful for treating a cardiovascular disease, cholesterol biosynthesis inhibitors, cholesterol absorption inhibitors, bile acid sequestrants, probucol derivatives, IBAT inhibitors, nicotinic acid receptor (NAR) agonists, ACAT inhibitors, cholesteryl ester transfer protein (CETP) inhibitors, low-density lipoprotein (LDL) activators, fish oil, water-soluble fibers, plant sterols, plant stanols, fatty acid esters of plant stanols, or any combination of two or more of these additional therapeutic agents.

Non-limiting examples of anti-obesity agents useful in the present methods for treating a Condition include CB1 antagonists or inverse agonists such as rimonabant, neuropeptide Y antagonists, MCR4 agonists, MCH receptor antagonists, histamine $H_3$ receptor antagonists or inverse agonists, metabolic rate enhancers, nutrient absorption inhibitors, leptin, appetite suppressants and lipase inhibitors.

Non-limiting examples of appetite suppressant agents useful in the present methods for treating or preventing a Condition include cannabinoid receptor 1 ($CB_1$) antagonists or inverse agonists (e.g., rimonabant); Neuropeptide Y (NPY1, NPY2, NPY4 and NPY5) antagonists; metabotropic glutamate subtype 5 receptor (mGluR5) antagonists (e.g., 2-methyl-6-(phenylethynyl)-pyridine and 3[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramine); glucagon-like peptide 1 (GLP-1) agonists; topiramate; and phytopharm compound 57.

Non-limiting examples of metabolic rate enhancers useful in the present methods for treating or preventing a Condition include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, amrinone, milrinone, cilostamide, rolipram and cilomilast); thyroid hormone β agonists; uncoupling protein activators (UCP-1,2 or 3) (e.g., phytanic acid, 4-[(E)-2-(5,6,7,8-tetramethyl-2-naphthalenyl)-1-propenyl]benzoic acid and retinoic acid); acyl-estrogens (e.g., oleoyl-estrone); glucocorticoid antagonists; 11-beta hydroxy steroid dehydrogenase type 1 (11β HSD-1) inhibitors; melanocortin-3 receptor (Mc3r) agonists; and stearoyl-CoA desaturase-1 (SCD-1) compounds.

Non-limiting examples of nutrient absorption inhibitors useful in the present methods for treating or preventing a Condition include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Non-limiting examples of cholesterol biosynthesis inhibitors useful in the present methods for treating or preventing a Condition include HMG-CoA reductase inhibitors, squalene synthase inhibitors, squalene epoxidase inhibitors and mixtures thereof.

Non-limiting examples of cholesterol absorption inhibitors useful in the present methods for treating or preventing a Condition include ezetimibe and other compounds suitable for the same purpose. In one embodiment, the cholesterol absorption inhibitor is ezetimibe.

HMG-CoA reductase inhibitors useful in the present methods for treating or preventing a Condition include, but are not limited to, statins such as lovastatin, pravastatin, fluvastatin, simvastatin, atorvastatin, cerivastatin, CI-981, resuvastatin, rivastatin, pitavastatin, rosuvastatin or L-659,699 ((E,E)-11-[3'R-(hydroxy-methyl)-4'-oxo-2'R-oxetanyl]-3,5,7R-trimethyl-2,4-undecadienoic acid).

Squalene synthesis inhibitors useful in the present methods for treating or preventing a Condition include, but are not limited to, squalene synthetase inhibitors; squalestatin 1; and squalene epoxidase inhibitors, such as NB-598 ((E)-N-ethyl-N-(6,6-dimethyl-2-hepten-4-ynyl)-3-[(3,3'-bithiophen-5-yl)methoxy]benzene-methanamine hydrochloride).

Bile acid sequestrants useful in the present methods for treating or preventing a Condition include, but are not limited to, cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Suitable inorganic cholesterol sequestrants include bismuth salicylate plus montmorillonite clay, aluminum hydroxide and calcium carbonate antacids.

Probucol derivatives useful in the present methods for treating or preventing a Condition include, but are not limited to, AGM 067 and others disclosed in U.S. Pat. Nos. 6,121,319 and 6,147,250.

IBAT inhibitors useful in the present methods for treating or preventing a Condition include, but are not limited to, benzothiepines such as therapeutic compounds comprising a 2,3,4,5-tetrahydro-1-benzothiepine 1,1-dioxide structure such as are disclosed in International Publication No. WO 00/38727.

Nicotinic acid receptor agonists useful in the present methods for treating or preventing a Condition include, but are not limited to, those having a pyridine-3-carboxylate structure or a pyrazine-2-carboxylate structure, including acid forms, salts, esters, zwitterions and tautomers, where available. Other examples of nicotinic acid receptor agonists useful in the present methods include nicotinic acid, niceritrol, nicofuranose and acipimox. An example of a suitable nicotinic acid product is NIASPAN® (niacin extended-release tablets) which are available from Kos Pharmaceuticals, Inc. (Cranbury, N.J.).

ACAT inhibitors useful in the present methods for treating or preventing a Condition include, but are not limited to, avasimibe, HL-004, lecimibide and CL-277082 (N-(2,4-difluorophenyl)-N-[[4-(2,2-dimethylpropyl)phenyl]-methyl]-N-heptylurea). See P. Chang et al., "Current, New and Future Treatments in Dyslipidaemia and Atherosclerosis", *Drugs* 2000 July; 60(1); 55-93, which is incorporated by reference herein.

CETP inhibitors useful in the present methods for treating or preventing a Condition include, but are not limited to, those disclosed in International Publication No. WO 00/38721 and U.S. Pat. No. 6,147,090, which are incorporated herein by reference.

LDL-receptor activators useful in the present methods for treating or preventing a Condition include, but are not limited to, include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", *Arterioscler. Thromb.* 1993; 13:1005-12.

Natural water-soluble fibers useful in the present methods for treating or preventing a Condition include, but are not limited to, psyllium, guar, oat and pectin.

Fatty acid esters of plant stanols useful in the present methods for treating or preventing a Condition include, but are not limited to, the sitostanol ester used in BENECOL® margarine.

Non-limiting examples of antidiabetic agents useful in the present methods for treating a Condition include insulin sensitizers, β-glucosidase inhibitors, DPP-IV inhibitors, insulin secretagogues, hepatic glucose output lowering compounds, antihypertensive agents, sodium glucose uptake transporter 2 (SGLT-2) inhibitors, insulin and insulin-containing compositions, and anti-obesity agents as set forth above.

In one embodiment, the antidiabetic agent is an insulin secretagogue. In one embodiment, the insulin secretagogue is a sulfonylurea.

Non-limiting examples of sulfonylureas useful in the present methods include glipizide, tolbutamide, glyburide, glimepiride, chlorpropamide, acetohexamide, gliamilide, gliclazide, gliquidone, glibenclamide and tolazamide.

In another embodiment, the insulin secretagogue is a meglitinide.

Non-limiting examples of meglitinides useful in the present methods for treating a Condition include repaglinide, mitiglinide, and nateglinide.

In still another embodiment, the insulin secretagogue is GLP-1 or a GLP-1 mimetic.

Non-limiting examples of GLP-1 mimetics useful in the present methods include Byetta-Exanatide, Liraglutinide, CJC-1131 (ConjuChem, Exanatide-LAR (Amylin), BIM-51077 (Ipsen/LaRoche), ZP-10 (Zealand Pharmaceuticals), and compounds disclosed in International Publication No. WO 00/07617.

Other non-limiting examples of insulin secretagogues useful in the present methods include exendin, GIP and secretin.

In another embodiment, the antidiabetic agent is an insulin sensitizer.

Non-limiting examples of insulin sensitizers useful in the present methods include PPAR activators or agonists, such as troglitazone, rosiglitazone, pioglitazone and englitazone; biguanidines such as metformin and phenformin; PTP-1B inhibitors; and glucokinase activators.

In another embodiment, the antidiabetic agent is a β-Glucosidase inhibitor.

Non-limiting examples of β-Glucosidase inhibitors useful the present methods include miglitol, acarbose, and voglibose.

In another embodiment, the antidiabetic agent is an hepatic glucose output lowering agent.

Non-limiting examples of hepatic glucose output lowering agents useful in the present methods include Glucophage and Glucophage XR.

In yet another embodiment, the antidiabetic agent is insulin, including all formulations of insulin, such as long acting and short acting forms of insulin.

Non-limiting examples of orally administrable insulin and insulin containing compositions include AL-401 from Autoimmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In another embodiment, the antidiabetic agent is a DPP-IV inhibitor.

Non-limiting examples of DPP-IV inhibitors useful in the present methods include sitagliptin, saxagliptin, denagliptin, vildagliptin, alogliptin, alogliptin benzoate, Galvus (Novartis), ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer) and RO-0730699 (Roche).

In a further embodiment, the antidiabetic agent is a SGLT-2 inhibitor.

Non-limiting examples of SGLT-2 inhibitors useful in the present methods include dapagliflozin and sergliflozin, AVE2268 (Sanofi-Aventis) and T-1095 (Tanabe Seiyaku).

Non-limiting examples of antihypertensive agents useful in the present methods for treating a Condition include β-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

In one embodiment, the antidiabetic agent is an agent that slows or blocks the breakdown of starches and certain sugars.

Non-limiting examples of antidiabetic agents that slow or block the breakdown of starches and certain sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in International Publication No. WO 00/07617.

Other specific additional therapeutic agents useful in the present methods for treating or preventing a Condition include, but are not limited to, rimonabant, 2-methyl-6-(phenylethynyl)-pyridine, 3[(2-methyl-1,4-thiazol-4-yl)ethynyl]pyridine, Melanotan-II, dexfenfluramine, fluoxetine, paroxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

In one embodiment, the present combination therapies for treating or preventing diabetes comprise administering a compound of formula (I), an antidiabetic agent and/or an antiobesity agent.

In another embodiment, the present combination therapies for treating or preventing diabetes comprise administering a compound of formula (I) and an antidiabetic agent.

In another embodiment, the present combination therapies for treating or preventing diabetes comprise administering a compound of formula (I) and an anti-obesity agent.

In one embodiment, the present combination therapies for treating or preventing obesity comprise administering a compound of formula (I), an antidiabetic agent and/or an antiobesity agent.

In another embodiment, the present combination therapies for treating or preventing obesity comprise administering a compound of formula (I) and an antidiabetic agent.

In another embodiment, the present combination therapies for treating or preventing obesity comprise administering a compound of formula (I) and an anti-obesity agent.

In one embodiment, the present combination therapies for treating or preventing metabolic syndrome comprise administering a compound of formula (I) and one or more additional therapeutic agents selected from: anti-obesity agents, antidiabetic agents, any agent useful for treating metabolic syndrome, any agent useful for treating a cardiovascular disease, cholesterol biosynthesis inhibitors, sterol absorption inhibitors, bile acid sequestrants, probucol derivatives, IBAT inhibitors, nicotinic acid receptor (NAR) agonists, ACAT inhibitors, cholesteryl ester transfer proten (CETP) inhibitors, low-density lipoprotein (LDL) activators, fish oil, water-soluble fibers, plant sterols, plant stanols and fatty acid esters of plant stanols.

In one embodiment, the additional therapeutic agent is a cholesterol biosynthesis inhibitor. In another embodiment, the cholesterol biosynthesis inhibitor is an HMG-CoA reductase inhibitor. In another embodiment, the HMG-CoA reductase inhibitor is a statin. In another embodiment, the statin is lovastatin, pravastatin, simvastatin or atorvastatin.

In one embodiment, the additional therapeutic agent is a cholesterol absorption inhibitor. In another embodiment, the cholesterol absorption inhibitor is ezetimibe. In another embodiment, the cholesterol absorption inhibitor is a squalene synthetase inhibitor. In another embodiment, the cholesterol absorption inhibitor is a squalene epoxidase inhibitor.

In one embodiment, the additional therapeutic agent comprises a cholesterol absorption inhibitor and a cholesterol biosynthesis inhibitor. In another embodiment, the additional therapeutic agent comprises a cholesterol absorption inhibitor and a statin. In another embodiment, the additional therapeutic agent comprises ezetimibe and a statin. In another embodiment, the additional therapeutic agent comprises ezetimibe and simvastatin.

In one embodiment, the present combination therapies for treating or preventing metabolic syndrome comprise administering a compound of formula (I), an antidiabetic agent and/or an antiobesity agent.

In another embodiment, the present combination therapies for treating or preventing metabolic syndrome comprise administering a compound of formula (I) and an antidiabetic agent.

In another embodiment, the present combination therapies for treating or preventing metabolic syndrome comprise administering a compound of formula (I) and an anti-obesity agent.

In one embodiment, the present combination therapies for treating or preventing a cardiovascular disease comprise administering one or more compounds of formula (I), and an additional agent useful for treating or preventing a cardiovascular disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more compounds of Formula I are administered during a time when the additional therapeutic agent(s) exert their prophylactic or therapeutic effect, or vice versa.

In another embodiment, the one or more compounds of Formula I and the additional therapeutic agent(s) are administered in doses commonly employed when such agents are used as monotherapy for treating a Condition.

In another embodiment, the one or more compounds of Formula I and the additional therapeutic agent(s) are administered in doses lower than the doses commonly employed when such agents are used as monotherapy for treating a Condition.

In still another embodiment, the one or more compounds of Formula I and the additional therapeutic agent(s) act synergistically and are administered in doses lower than the doses commonly employed when such agents are used as monotherapy for treating a Condition.

In one embodiment, the one or more compounds of Formula I and the additional therapeutic agent(s) are present in the same composition. In one embodiment, this composition is suitable for oral administration. In another embodiment, this composition is suitable for intravenous administration.

The one or more compounds of Formula I and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more compounds of Formula I and the additional therapeutic agent(s) may inhibit the resistance of a Condition to these agents.

In one embodiment, when the patient is treated for diabetes or a diabetic complication, the additional therapeutic agent is an antidiabetic agent which is not a compound of Formula I.

In another embodiment, the additional therapeutic agent is an agent useful for reducing any potential side effect of a compound of Formula I. Such potential side effects include, but are not limited to, nausea, vomiting, headache, fever, lethargy, muscle aches, diarrhea, general pain, and pain at an injection site.

The pharmacological properties of the compounds of this invention may be confirmed by a number of pharmacological assays. The exemplified pharmacological assays which are described later have been carried out with the compounds according to the invention and their salts.

The invention is also directed to pharmaceutical compositions which comprise at least one compound of Formula I, or a pharmaceutically acceptable salt, solvate, ester or prodrug of said compound and at least one pharmaceutically acceptable carrier.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium state, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Penn.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose. The compounds of this invention may also be delivered subcutaneously.

Preferably the compound is administered orally.

Preferably, the pharmaceutical preparation is in a unit dosage form. In such form, the preparation is subdivided into suitable sized unit doses containing appropriate quantities of the active component, e.g. an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt, solvate, ester or prodrug of said compound and a pharmaceutically acceptable carrier, vehicle or diluent.

Yet another aspect of this invention is a kit comprising an amount of at least one compound of Formula I, or a pharmaceutically acceptable salt, solvate, ester or prodrug of said compound and an amount of at least one therapeutic agent listed above, wherein the amounts of the two or more ingredients result in a desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Variant VXR-200 (200 MHz, $^1$H), Varian Gemini-300 (300 MHZ), Varian Mercury VX-400 (400 MHz), or Bruker-Biospin AV-500(500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:
Me=methyl
Et=ethyl
Pr=propyl
Bu=butyl
Ph=phenyl
Ac=acetyl
μl=microliters
AcOEt or EtOAc=ethyl acetate
AcOH or HOAc=acetic acid
ACN=acetonitrile
atm=atmosphere
Boc or BOC=tert-butoxycarbonyl
DCE=dichloroethane
DCM or $CH_2Cl_2$=dichloromethane DIPEA=diisopropylethylamine
DMAP=4-dimethylaminopyridine
DMF=dimethylformamide
DMS=dimethylsulfide
DMSO=dimethyl sulfoxide
EDCI=1-(3-dimethylaminopropyl)-3-ethylcarbodiimine
Fmoc or FMOC=9-fluorenylmethoxycarbonyl
g=grams
h=hour
hal=halogen
HOBt=1-hydroxybenzotriazole
LAH=lithium aluminum hydride
LCMS=liquid chromatography mass spectrometry
min=minute
mg=milligrams
mL=milliliters
mmol=millimoles
MCPBA=3-chloroperoxybenzoic acid
MeOH=methanol
MS=mass spectrometry
NMR=nuclear magnetic resonance spectroscopy
RT or rt=room temperature (ambient, about 25° C.)
TEA or Et$_3$N=triethylamine
TFA=trifluoroacetic acid
THF=tetrahydrofuran
TLC=thin layer chromatography
TMS=trimethylsilyl
Tr=triphenylmethyl

EXAMPLES

The compounds of this invention can be prepared as generally described in the Preparation Schemes, and the following examples.

Synthesis of Class A Compounds

Synthesis of Compound 1
To a solution of 8-aza-bicyclo[3.2.1]octane-3-one hydrochloride (0.30 g, 1.86 mmol) in dichloromethane (25 mL) was added Hünig's base (1.32 mL, 7.44 mmol) followed by 4-tert-butyl-benzenesulfonyl chloride (0.65 g, 2.80 mmol). The reaction mixture was stirred under an atmosphere of nitrogen for 16 h after which it was quenched with saturated ammonium chloride solution and extracted with dichloromethane. The organic phase was washed with water and brine, dried (MgSO$_4$), filtered, and concentrated. Purification by column chromatography (20% ethyl acetate in hexane) afforded Compound 1 (0.45 g, 76% yield).

Synthesis of Compound 2 and Compound 3
To a solution of Compound 1 (100 mg, 0.31 mmol) in 10 mL methanol was added sodium borohydride (36 mg, 0.93 mmol). The reaction was stirred at room temperature for 30 minutes after which it was quenched with saturated ammonium chloride solution and extracted with dichloromethane. The organic fraction was dried (Na$_2$SO$_4$), filtered, and concentrated to give a yellow oil. Purification by preparative TLC (30% ethyl acetate in hexane) afforded a mixture of Compound 2 (less polar, 40 mg, 40% yield) and Compound 3 (more polar, 60 mg, 60% yield).

Synthesis of Compound 4
To a solution of Compound 3 (10.0 mg, 0.03 mmol) in 1 mL DMF was added 60% NaH (4.8 mg, 0.12 mmol) followed by iodomethane (13.0 mg, 0.09 mmol). The reaction was stirred at room temperature for 3 h after which it was quenched with water and extracted with ethyl acetate. Purification by preparative TLC (30% ethyl acetate in hexane) afforded Compound 4 (7 mg, 67% yield).

Synthesis of Compound 5
To a solution of Compound 3 (15.0 mg, 0.05 mmol) in 1 mL DMF was added 60% NaH (3.0 mg, 0.07 mmol) followed by

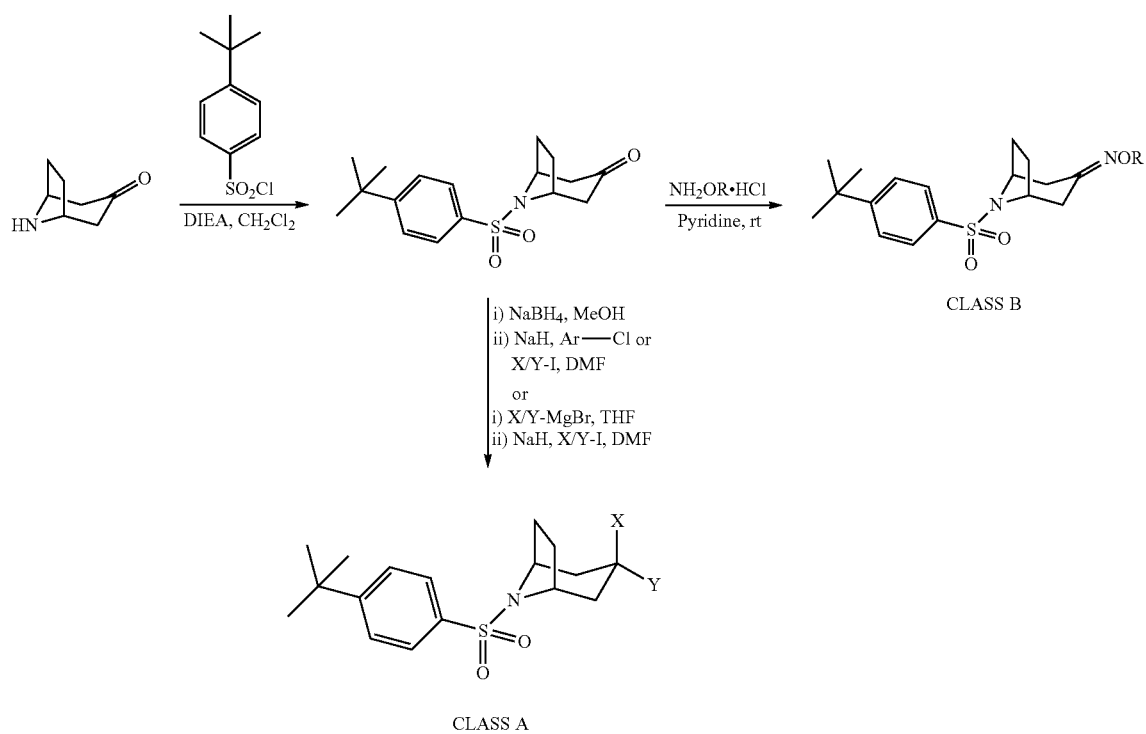

Preparation Scheme 1

6-chloro-nicotinonitrile (8.0 mg, 0.06 mmol). The reaction was stirred at room temperature for 16 h after which it was quenched with water and extracted with ethyl acetate. Purification by preparative TLC (30% ethyl acetate in hexane) afforded Compound 5 (7 mg, 36% yield).

Synthesis of Compound 6

Compound 6 was synthesized from Compound 2 in the same manner as described for the synthesis of Compound 5.

Synthesis of Compound 7

Compound 7 was synthesized from Compound 2 in the same manner as described for the synthesis of Compound 4.

Synthesis of Compound 8

Compound 8 was synthesized from Compound 3 in the same manner as described for the synthesis of Compound 4 but using iodoethane instead of iodomethane.

Synthesis of Compound 10

To a solution of Compound 1 (100 mg, 0.31 mmol) in 7 mL THF was added methylmagnesium bromide (3M in ether, 0.31 mL, 0.93 mmol). The reaction was stirred at room temperature for 5 h after which it was quenched with saturated ammonium chloride solution and extracted with ethyl acetate. The organic fraction was dried ($Na_2SO_4$), filtered, and concentrated to give a yellow oil. Purification by preparative TLC (30% ethyl acetate in hexane) afforded Compound 10 (100 mg, 96% yield).

Synthesis of Compound 9

To a solution of Compound 10 (100 mg, 0.31 mmol) in 4 mL DMF was added 60% NaH (50.0 mg, 1.2 mmol) and the reaction was stirred at room temperature for 2 h after which iodomethane (0.1 mL, 1.2 mmol). After 1 h the reaction was quenched with water and extracted with ethyl acetate. Purification by preparative TLC (30% ethyl acetate in hexane) afforded Compound 9 (100 mg, 96% yield).

Synthesis of Compound 11 and Compound 12

To an ice-cold solution of Compound 1 (50 mg, 0.16 mmol) in 5 mL THF was added (trifluoromethyl)-trimethylsilane (35.0 μL, 0.24 mmol) followed by TBAF (1 M in THF, 0.02 mL, 0.02 mmol). The reaction was warmed to room temperature and stirred for 2 h after which it was quenched with 1N aqueous HCl solution and extracted with ethyl acetate. The organic fraction was dried ($Na_2SO_4$), filtered, and concentrated to give a yellow oil. Purification by preparative TLC (30% ethyl acetate in hexane) afforded a mixture of Compound 11 (less polar, 20 mg, 33% yield) and Compound 12 (more polar, 22 mg, 34% yield).

Synthesis of Compound 13

Compound 13 was synthesized from Compound 11 in the same manner as described for the synthesis of Compound 9.

Synthesis of Compound 14

Compound 14 was synthesized from Compound 12 in the same manner as described for the synthesis of Compound 9.

Synthesis of Compound 15

Compound 15 was synthesized from Compound 1 in the same manner as described for the synthesis of Compound 10 but using benzylmagnesium bromide instead of methylmagnesium bromide.

Synthesis of Compound 16

Compound 16 was synthesized from Compound 1 in the same manner as described for the synthesis of Compound 10 but using phenylmagnesium bromide instead of methylmagnesium bromide.

Synthesis of Class B compounds

To a solution of Compound 1 (50 mg, 0.16 mmol) in 2 mL pyridine was added the corresponding O-substituted hydroxylamine hydrochloride (0.80 mmol) and the reaction mixture was stirred at room temperature for 16 h. After removing the solvent under reduced pressure, the resulting residue was purified by preparative TLC (30% ethyl acetate in hexane) to afford the corresponding class-B oxime.

Preparation Scheme 2

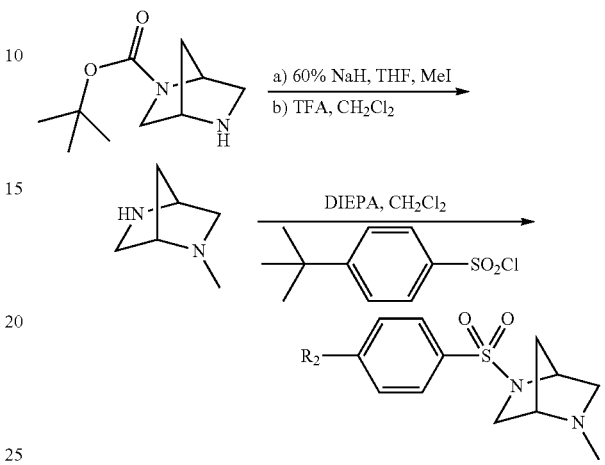

Synthesis of Compounds 20-24

To a solution of (1S,4S)-2-BOC-2,5-diazabicyclo[2.2.1]heptane (0.50 g, 2.52 mmol) in 30 mL THF at 0° C. was added 60% NaH (0.12 g, 3.02 mmol) followed by MeI (0.17 mL, 2.77 mmol). The reaction was warmed to room temperature and stirred for 2 h after which it was quenched with water and extracted with ethyl acetate. The organic fractions were combined, dried ($Na_2SO_4$), filtered, and concentrated to obtain an oil which was used for the next step without purification.

To the crude material from above in 40 mL dichloromethane was added 10 mL TFA at 0° C. The reaction was warmed to room temperature and stirred for 3 h after which it was concentrated under reduced pressure. The resulting oily residue was diluted with dichloromethane and washed with aqueous 1M NaOH solution. The organic fractions were combined, dried ($Na_2SO_4$), filtered, and concentrated to obtain (1S,4S)-2-methyl-2,5-diazabicyclo[2.2.1]heptane which was used for the next step without purification.

To a solution of (1S,4S)-2-methyl-2,5-diazabicyclo[2.2.1]heptane (0.02 g, 0.18 mmol) in 1 mL dichloromethane was added diisopropylethyl amine (3.0 equiv) followed by the commercially available sulfonyl chloride (1.5 equiv). The reaction was stirred at room temperature for 48 h after which it was concentrated and purified by preparative TLC (5% MeOH in dichloromethane) to afford the desired sulfonamide (20-60% yield).

Compounds 20-24 were Prepared Using the Above Described Procedure.

Preparation Scheme 3

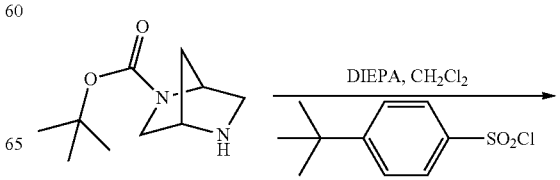

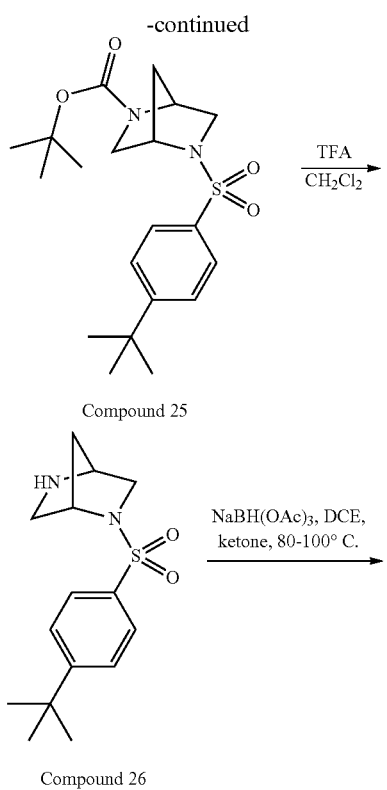

Compound 25

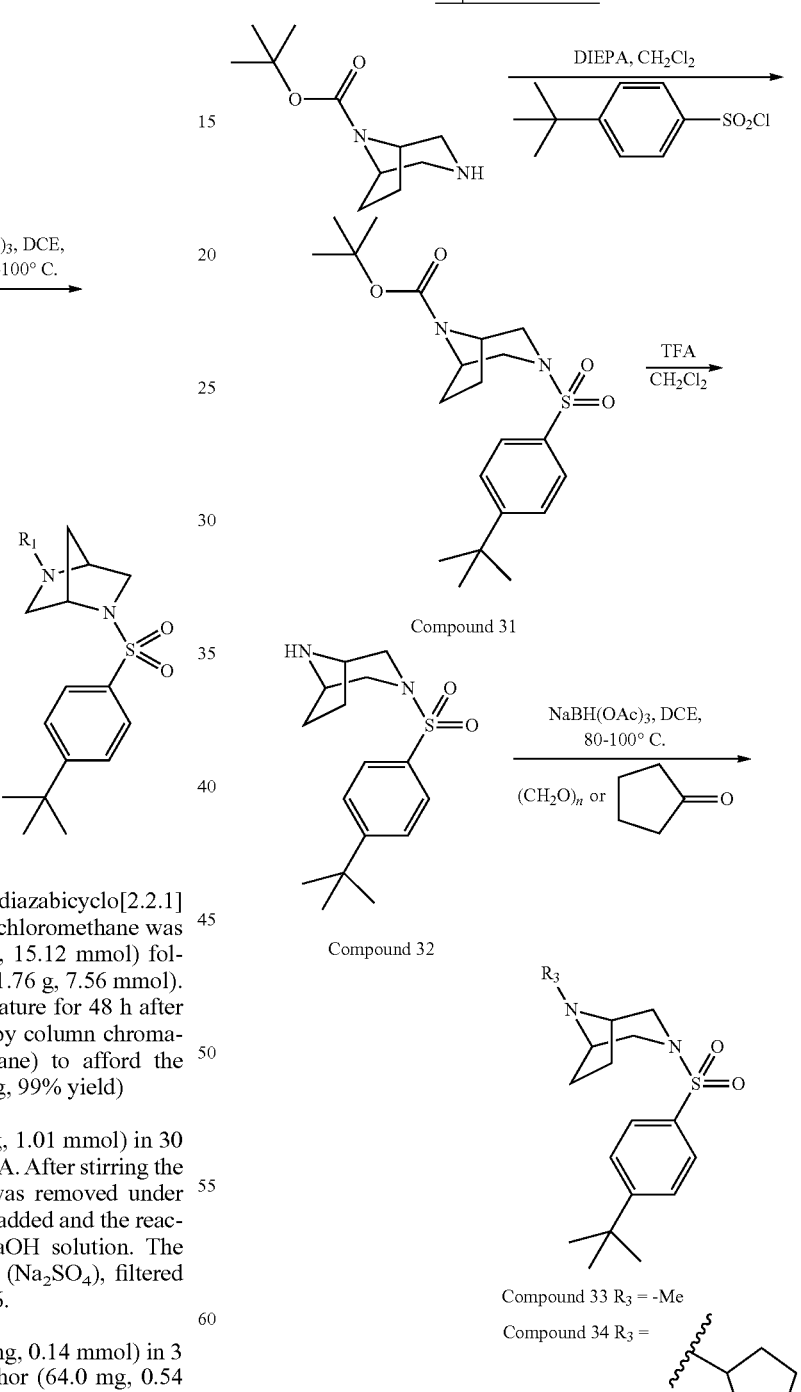

Synthesis of Compound 25

To a solution of (1S,4S)-2-BOC-2,5-diazabicyclo[2.2.1]heptane (1.0 g, 5.04 mmol) in 50 mL dichloromethane was added diisopropylethyl amine (2.63 mL, 15.12 mmol) followed by 4-tert-butyl-sulfonyl chloride (1.76 g, 7.56 mmol). The reaction was stirred at room temperature for 48 h after which it was concentrated and purified by column chromatography (5% MeOH in dichloromethane) to afford the desired sulfonamide Compound 25 (2.0 g, 99% yield)

Synthesis of Compound 26

To a solution of Compound 25 (0.40 g, 1.01 mmol) in 30 mL dichloromethane was added 6 mL TFA. After stirring the reaction mixture for 1 h, the solvent was removed under reduced pressure. Dichloromethane was added and the reaction was washed with aqueous 1M NaOH solution. The organic fractions were combined, dried ($Na_2SO_4$), filtered and concentrated to obtain Compound 26.

Synthesis of Compounds 27 and 28

To a solution of Compound 26 (40.0 mg, 0.14 mmol) in 3 mL dichloroethane was added norcamphor (64.0 mg, 0.54 mmol) followed by sodium triacetoxyborohydride (120.0 mg, 0.54 mmol). The reaction mixture was stirred at 80° C. for 16 h, after which it was cooled to room temperature. Aqueous 1M NaOH solution was added and the reaction was extracted with dichloromethane. Purification by preparative TLC (5% MeOH in dichloromethane) afforded Compound 27 (less polar, 8.0 mg) and Compound 28 (more polar, 8.5 mg).

Synthesis of Compounds 29 and 30

Compounds 29 and 30 were synthesized from Compound 26 in a similar manner as described for the synthesis of Compound 27 but using cyclohexanone and cyclopentanone respectively instead of norcamphor.

Compound 31 was synthesized from 3,8-diaza-bicyclo[3.2.1]octane-8-carboxylic acid tert-butyl ester in a similar manner as described for the synthesis of Compound 25.

Compound 32 was synthesized from Compound 31 in a similar manner as described for the synthesis of Compound 26.

Compound 33 was synthesized from Compound 32 in a similar manner as described for the synthesis of Compound 30 but using paraformaldehyde instead of cyclopentanone.

Compound 34 was synthesized from Compound 32 in a similar manner as described for the synthesis of Compound 30.

Measurement of 11β-HSD1 Activity

11β-HSD1 enzymatic activity was measured in a 50 µl reaction containing 20 mM $NaPO_4$ pH 7.5, 0.1 mM $MgCl_2$, 3 mM NADPH (prepared fresh daily), 125 nM $^3$H-cortisone (American Radiochemicals) and 0.5 µg membrane. The reaction was incubated at room temperature for 1 hr before it was stopped by addition of 50 µM buffer containing 20 mM $NaPO_4$ pH 7.5, 30 µM 18β-glycyrrhetinic acid, 1 µg/ml monoclonal anti-cortisol antibody (Biosource) and 2 mg/ml anti-mouse antibody coated scintillation proximity assay (SPA) beads (Amersham Bioscience). The mixture was incubated at room temperature for 2 hrs with vigorous shaking and analyzed on TopCount scintillation counter.

Compounds according to the present invention showed activity against 11β-HSD1 in this assay.

In Vivo Screen for Inhibition of 11β-HSD-1

Lean male C57BI/6N mice were orally dosed with a solution of dexamethasone (0.5 mg/kg) and test agent or vehicle (20% HP☐CD (10 ml/kg)). One hour later, cortisone was administered (1 mg/kg sc in sesame oil). One hour after cortisone administration, animals were euthanized for blood collection, and plasma cortisol levels were determined with a commercially available ELISA.

Compounds according to the present invention inhibited 11β-HSD1 in this screen.

Table 2 shows 11β-HSD-1 activity of representative compounds of this invention. The table and the compounds therein are not intended, nor should they be construed, to limit this invention in any manner whatsoever.

TABLE 2

| Compound No. | Human 11-β-HSD1 $IC_{50}$ (nM) | Mouse 11-β-HSD1 $IC_{50}$ (nM) | Mouse cort. challenge % I @ 30 mpk |
|---|---|---|---|
| 6 | 413 | 5588 | |
| 16 | 1623 | 138 | |
| 15 | 740 | 114 | |
| 2 | 30 | 28 | 24 |
| 7 | 69 | 8 | |
| 10 | 19 | 41 | |
| 9 | 14 | 13 | 18 |
| 11 | 276 | 3 | |
| 13 | 356 | 32 | |
| 5 | >10,000 | 23848 | |
| 3 | 970 | 5 | |
| 4 | 37 | 5 | 57 |
| 8 | 114 | 2 | |
| 12 | 32 | 206 | |
| 14 | 48 | 43 | |
| 19 | 159 | 989 | |
| 18 | 860 | 103 | |
| 17 | 270 | 47 | |
| 20 | 109 | 357 | |
| 21 | 333 | 258 | |
| 22 | 3347 | 3091 | |
| 23 | 16065 | 8877 | |
| 24 | 11285 | 12111 | |
| 25 | 361 | 772 | |
| 26 | 4402 | 156 | |
| 27 | 75 | 31 | |

TABLE 2-continued

| Compound No. | Human 11-β-HSD1 $IC_{50}$ (nM) | Mouse 11-β-HSD1 $IC_{50}$ (nM) | Mouse cort. challenge % I @ 30 mpk |
|---|---|---|---|
| 28 | 77 | 8 | |
| 29 | 118 | 79 | |
| 30 | 40 | 1 | Inactive |
| 31 | 309 | 692 | |
| 32 | 547 | 54 | |
| 33 | 478 | 117 | |
| 34 | 137 | 3 | |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound selected from the group consisting of:

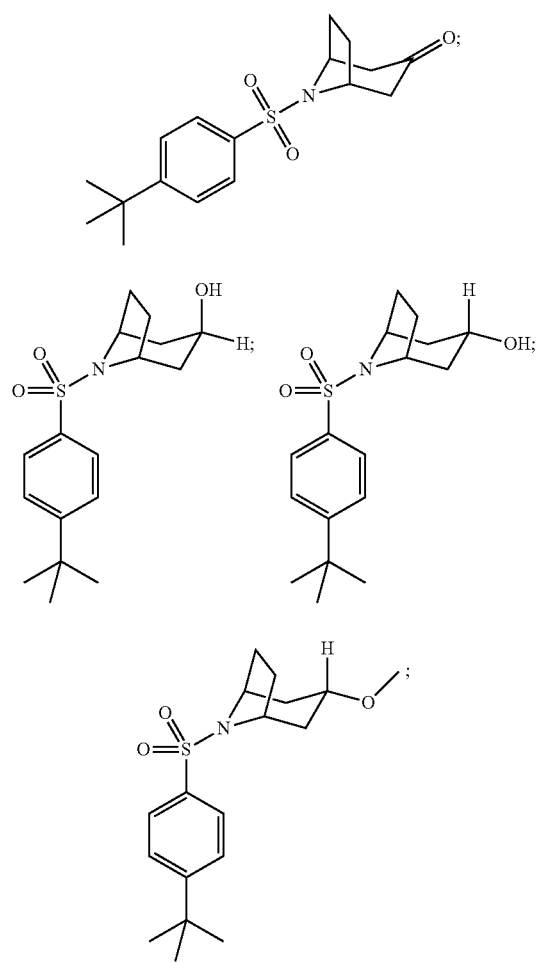

41
-continued
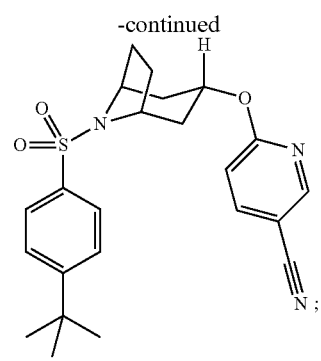
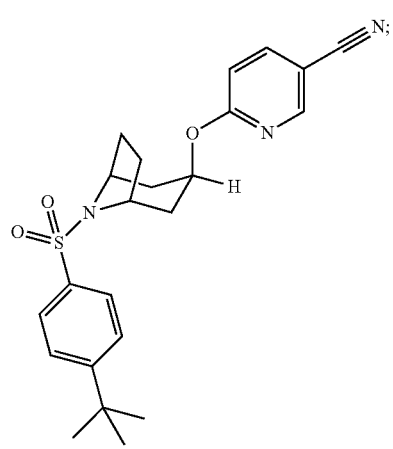
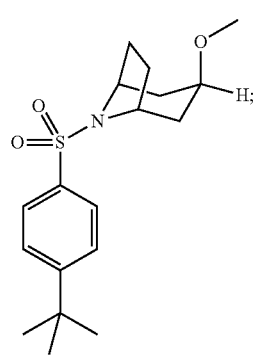
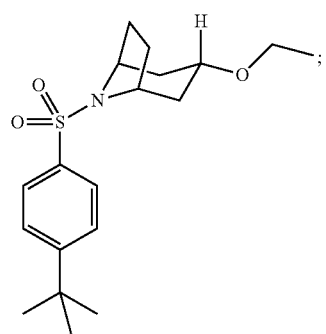
42
-continued
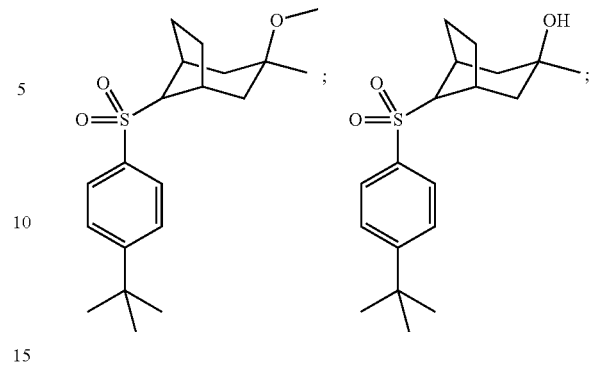
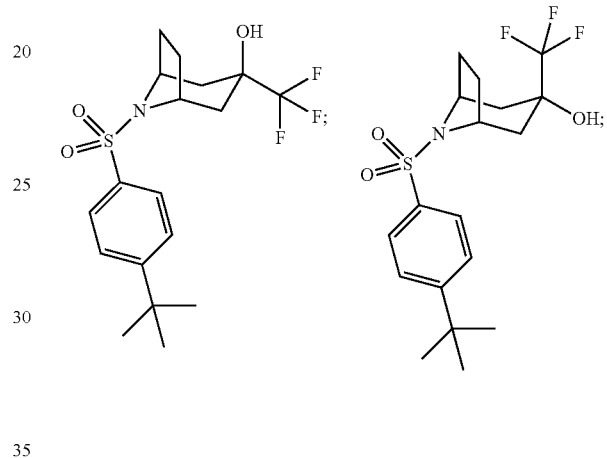
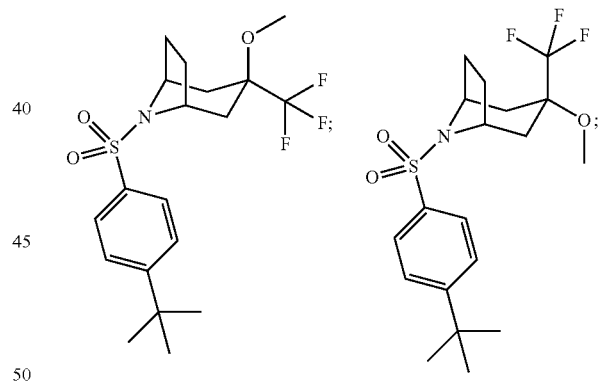
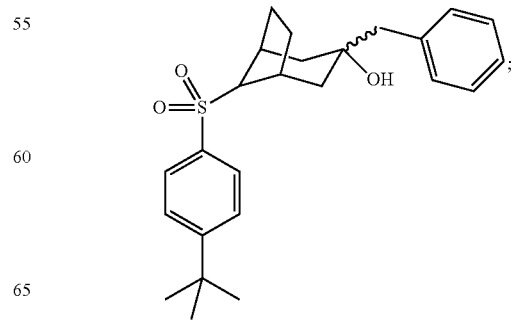

43
-continued
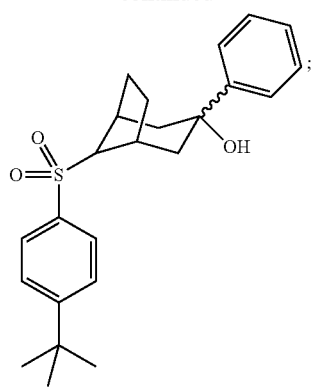
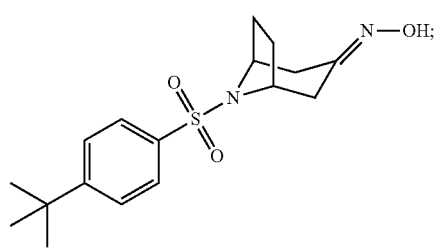
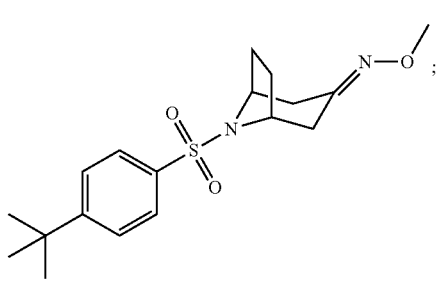
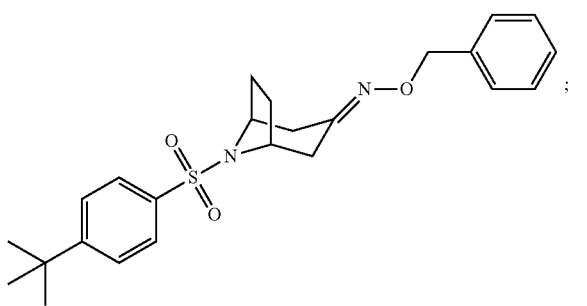
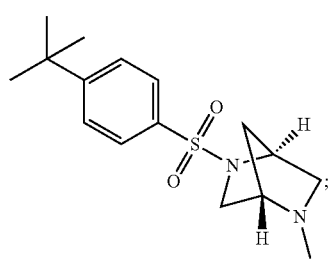
44
-continued
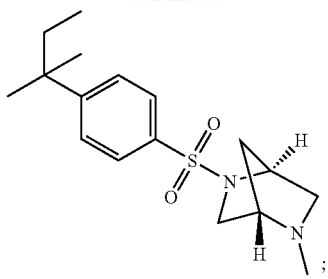
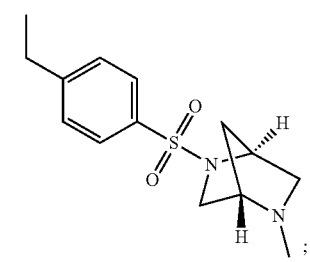
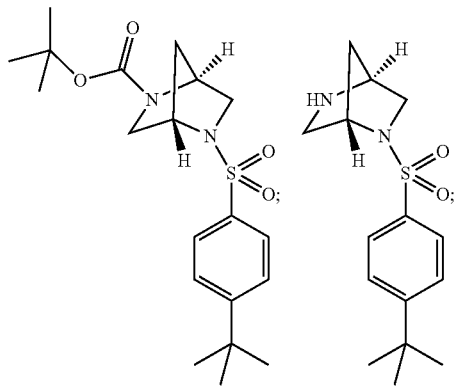
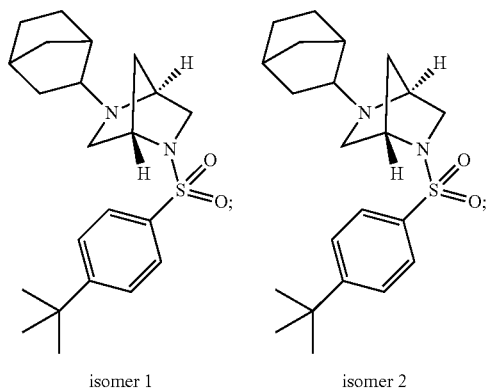
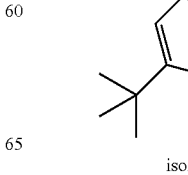
isomer 1                isomer 2

-continued
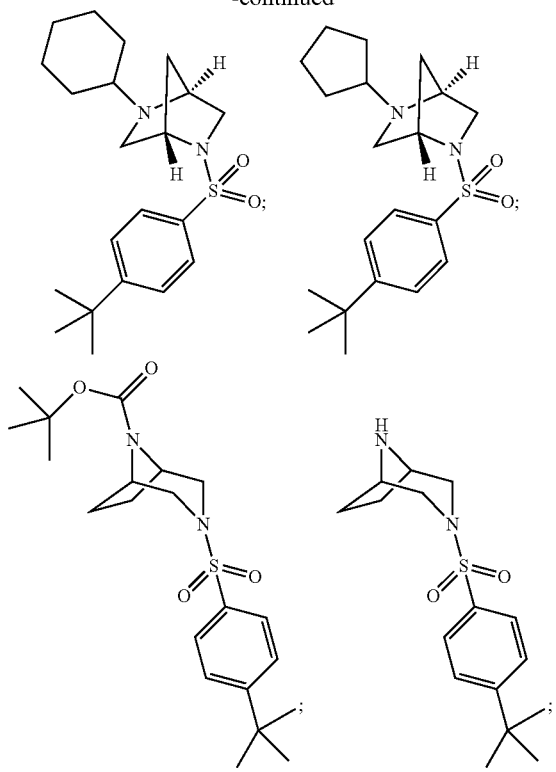
-continued
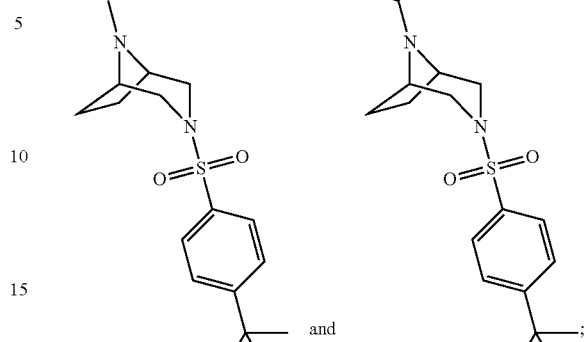
or a pharmaceutically acceptable salt thereof.
2. A pharmaceutical composition comprising at least one compound of claim 1, or a pharmaceutically acceptable salt thereof and at least one pharmaceutically acceptable carrier, adjuvant or vehicle.
* * * * *

UNITED STATES PATENT AND TRADEMARK OFFICE
CERTIFICATE OF CORRECTION

PATENT NO.        : 8,604,195 B2                                    Page 1 of 1
APPLICATION NO. : 12/672825
DATED             : December 10, 2013
INVENTOR(S)       : Shah et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 835 days.

Signed and Sealed this
Twenty-second Day of September, 2015

Michelle K. Lee
*Director of the United States Patent and Trademark Office*